United States Patent
Bading et al.

(10) Patent No.: US 10,104,852 B2
(45) Date of Patent: Oct. 23, 2018

(54) PLANTS AND SEEDS OF SORGHUM VARIETY GSV644454

(71) Applicant: Monsanto Technology LLC, St. Louis, MO (US)

(72) Inventors: Ryan S. Bading, Corpus Christi, TX (US); Miguel A. Gutierrez, O'Fallon, MO (US); Michael C. Lenz, Wichita, KS (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/460,016

(22) Filed: Mar. 15, 2017

(65) Prior Publication Data

US 2018/0263202 A1     Sep. 20, 2018

(51) Int. Cl.
| | | |
|---|---|---|
| *C12N 5/10* | (2006.01) | |
| *A01H 5/10* | (2018.01) | |
| *A01H 6/46* | (2018.01) | |

(52) U.S. Cl.
CPC ............ *A01H 5/10* (2013.01); *A01H 6/46* (2018.05)

(58) Field of Classification Search
CPC ....................................................... A01H 5/10
USPC ............................................................. 800/320
See application file for complete search history.

(56) References Cited

U.S. PATENT DOCUMENTS

| | | | |
|---|---|---|---|
| 5,523,520 | A | 6/1996 | Hunsperger et al. |
| 8,212,126 | B2 | 7/2012 | Bading et al. |
| 8,461,426 | B2 | 6/2013 | Bading et al. |
| 8,878,024 | B2 | 11/2014 | Bading et al. |
| 8,969,670 | B2 | 3/2015 | Lenz |
| 8,969,671 | B2 | 3/2015 | Bading et al. |
| 8,969,672 | B2 | 3/2015 | Lenz |
| 8,969,673 | B2 | 3/2015 | Lenz |
| 9,516,844 | B2 | 12/2016 | Bading et al. |
| 9,521,819 | B2 | 12/2016 | Lenz |
| 2010/0064382 | A1* | 3/2010 | Rooney .............. A01H 1/02 800/263 |

OTHER PUBLICATIONS

U.S. Appl. No. 15/007,887, filed Jan. 27, 2016, Bading et al.
U.S. Appl. No. 15/007,905, filed Jan. 27, 2016, Bading et al.
U.S. Appl. No. 15/460,019, filed Mar. 15, 2017, Bading et al.
U.S. Appl. No. 15/460,025, filed Mar. 15, 2017, Bading et al.
House, "A Guide to Breeding Sorghum," ICRISAT, Andhra Pradesh India pp. 27-149, 1985.
Allard, In: Principles of Plant Breeding, Chapter 6 through Chapter 9, University of California, Davis, California, John Wiley & Sons, New York, pp. 50-98, 1960.
Eshed et al., "Less-than-additive epistatic interactions of quantitative trait loci in tomato," *Genetics*, 143:1807-1817, 1996.
Fehr (ed.), In: Principles of Cultivar Development, vol. 1: Theory and Technique, pp. 360-376, 1987.
Kraft et al., "Linkage disequilibrium and fingerprinting in sugar beet," *Theor Appl Genet*, 101:323-326, 2000.
Poehlman, J.M. and Sleper, D.A., "Methods in Plant Breeding," In Breeding Field Crops, 4th ed., *Iowa State Press*, pp. 159-239, 1995.
Kresovich, S. et al., "Application of Cell and Tissue Culture Techniques for the Genetic Improvement of Sorghum" Advances in Agronomy, vol. 41, pp. 147-170 (1987).
Tomes, D.T., "Cereal Tissue & Cell Culture", Chapter 6, pp. 176-203. Martinus Hijnoff/Dr. W. Juns. Amtisdau, Bright & Jones (ed.) 1985.
Vanderlip, R.L., "How a Sorghum Plant Develops", Kansas State University Agricultural Experiment Station and Cooperative Extension Service, S-3 Jan. 1993 [online], http://www.ksre.ksu.edu/bookstore/pubs/s3.pdf.
Variety specific information as indicated in transmittal letter of Jun. 27, 2017 Information Disclosure Statement for U.S. Appl. No. 15/460,016.

* cited by examiner

*Primary Examiner* — Li Zheng
(74) *Attorney, Agent, or Firm* — Dentons US LLP

(57) ABSTRACT

According to the invention, there is provided seed and plants of the sorghum variety designated GSV644454. The invention thus relates to the plants, seeds and tissue cultures of the variety GSV644454, and to methods for producing a sorghum plant produced by crossing a sorghum plant of variety GSV644454 with itself or with another sorghum plant, such as a plant of another variety. The invention further relates to sorghum seeds and plants produced by crossing plants of variety GSV644454 with plants of another variety, such as another inbred line. The invention further relates to the inbred and hybrid genetic complements of plants of variety GSV644454.

20 Claims, No Drawings

PLANTS AND SEEDS OF SORGHUM VARIETY GSV644454

BACKGROUND OF THE INVENTION

Field of the Invention

The present invention relates generally to a new sorghum line, designated GSV644454, as well as to seed, plants, cultivars, and hybrids related thereto. The invention also relates to methods for producing sorghum seeds and plants from GSV644454.

SUMMARY OF THE INVENTION

In one aspect, the present invention provides a sorghum plant of the variety designated GSV644454. Also provided are sorghum plants having all of the morphological and physiological characteristics of the inbred sorghum variety GSV644454. The inbred sorghum plant of the invention may further comprise, or have, a cytoplasmic or nuclear factor that is capable of conferring male sterility or otherwise preventing self-pollination, such as by self-incompatibility. Parts of the sorghum plant of the present invention are also provided, for example, pollen obtained from an inbred plant and an ovule of the inbred plant.

The invention also concerns seed of the inbred sorghum variety GSV644454. The inbred sorghum seed of the invention may be provided as an essentially homogeneous population of inbred sorghum seed of the variety designated GSV644454. Essentially homogeneous populations of inbred seed are generally free from substantial numbers of other seed. Therefore, in the practice of the present invention, inbred seed generally forms at least about 97% of the total seed. The population of inbred sorghum seed of the invention may be particularly defined as being essentially free from hybrid seed. The inbred seed population may be separately grown to provide an essentially homogeneous population of inbred sorghum plants designated GSV644454.

In a further aspect of the invention, a composition is provided comprising a seed of sorghum variety GSV644454 comprised in plant seed growth media. In certain embodiments, the plant seed growth media is a soil or synthetic cultivation medium. In specific embodiments, the growth medium may be comprised in a container or may, for example, be soil in a field.

In another aspect of the invention, a plant of sorghum variety GSV644454 comprising an added heritable trait is provided. The heritable trait may comprise a genetic locus that is a dominant or recessive allele. In one embodiment of the invention, a plant of sorghum variety GSV644454 further comprising a single locus conversion in particular is provided. In specific embodiments of the invention, an added genetic locus confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring sorghum gene introduced into the genome of the variety by backcrossing, a natural or induced mutation, or a transgene introduced through genetic transformation techniques. When introduced through transformation, a genetic locus may comprise one or more transgenes integrated at a single chromosomal location.

In yet another aspect of the invention, an inbred sorghum plant of the variety designated GSV644454 is provided, wherein a cytoplasmically-inherited trait has been introduced into said inbred plant. Such cytoplasmically-inherited traits are passed to progeny through the female parent in a particular cross. An exemplary cytoplasmically-inherited trait is the male sterility trait. Cytoplasmic-male sterility (CMS) is a pollen abortion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus, and continue to be male sterile in the next generation. The male fertility of a CMS plant can be restored by a restorer version of the same variety, which must have the restorer gene(s) in the nucleus. With the restorer gene(s) in the nucleus, the offspring of the male-sterile plant can produce normal pollen grains and propagate. A cytoplasmically inherited trait may be a naturally occurring sorghum trait or a trait introduced through genetic transformation techniques.

In another aspect of the invention, a tissue culture of regenerable cells of a plant of variety GSV644454 is provided. The tissue culture will preferably be capable of regenerating plants capable of expressing all of the morphological and physiological characteristics of the variety, and of regenerating plants having substantially the same genotype as other plants of the variety. Examples of some of the morphological and physiological characteristics that may be assessed include characteristics related to yield, maturity, and nutritional quality. The regenerable cells in such tissue cultures will preferably be derived from embryos, meristematic cells, microspores, pollen, anthers, stigma, flowers, leaves, stalks, roots, root tips, seeds, or from callus or protoplasts derived from those tissues. Still further, the present invention provides sorghum plants regenerated from the tissue cultures of the invention, the plants having all of the morphological and physiological characteristics of variety GSV644454.

In yet another aspect of the invention, processes are provided for producing sorghum seeds or plants, which processes generally comprise crossing a first parent sorghum plant as a male or female parent with a second parent sorghum plant, wherein at least one of the first or second parent sorghum plants is a plant of the variety designated GSV644454. These processes may be further exemplified as processes for preparing hybrid sorghum seed or plants, wherein a first inbred sorghum plant is crossed with a second sorghum plant of a different, distinct variety to provide a hybrid that has, as one of its parents, the inbred sorghum plant variety GSV644454. In these processes, crossing will result in the production of seed. The seed production occurs regardless of whether the seed is collected or not.

In one embodiment of the invention, the first step in "crossing" comprises planting, preferably in pollinating proximity, seeds of a first and second parent sorghum plant, and preferably, seeds of a first inbred sorghum plant and a second, distinct inbred sorghum plant. Where the plants are not in pollinating proximity, pollination can nevertheless be accomplished by mechanically or naturally transferring a pollen.

A second step comprises cultivating or growing the seeds of said first and second parent sorghum plants into plants that bear flowers (sorghum bears both male and female flowers on the same anatomical structures on the same plant). A third step comprises preventing self-pollination of the plants, i.e., preventing the female flowers of a plant from being fertilized by any plant of the same variety, including the same plant. This is preferably done by emasculating the male flowers of the first or second parent sorghum plant, (i.e., physically removing the anthers from the florets prior to blooming of the flowers so as to prevent pollen production or preventing dehiscence of pollen from anthers by introduction and maintenance of a high humidity environment by bagging a panicle or portion of a panicle with a plastic bag prior to blooming). Self-incompatibility systems may also be used in some hybrid crops for the same purpose. Self-incompatible plants still shed viable pollen and can pollinate plants of other varieties but are incapable of pollinating themselves or other plants of the same variety.

The present invention also provides sorghum seed and plants produced by a process that comprises crossing a first parent sorghum plant with a second parent sorghum plant, wherein at least one of the first or second parent sorghum plants is a plant of the variety designated GSV644454. In one embodiment of the invention, sorghum seed and plants produced by the process are first generation ($F_1$) hybrid sorghum seed and plants produced by crossing an inbred in accordance with the invention with another, distinct inbred. The present invention further contemplates seed of an $F_1$ hybrid sorghum plant. Therefore, certain exemplary embodiments of the invention provide an $F_1$ hybrid sorghum plant and seed thereof.

In still yet another aspect of the invention, the genetic complement of the sorghum plant variety designated GSV644454 is provided. The phrase "genetic complement" is used to refer to the aggregate of nucleotide sequences, the expression of which sequences defines the phenotype of, in the present case, a sorghum plant, or a cell or tissue of that plant. A genetic complement thus represents the genetic makeup of an inbred cell, tissue or plant, and a hybrid genetic complement represents the genetic makeup of a hybrid cell, tissue or plant. The invention thus provides sorghum plant cells that have a genetic complement in accordance with the inbred sorghum plant cells disclosed herein, and plants, seeds and diploid plants containing such cells.

Plant genetic complements may be assessed by genetic marker profiles, and by the expression of phenotypic traits that are characteristic of the expression of the genetic complement, e.g., isozyme typing profiles. It is understood that variety GSV644454 could be identified by any of the many well known techniques such as, for example, Simple Sequence Length Polymorphisms (SSLPs) (Williams et al., *Nucleic Acids Res.*, 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In still yet another aspect, the present invention provides hybrid genetic complements, as represented by sorghum plant cells, tissues, plants, and seeds, formed by the combination of a haploid genetic complement of a sorghum plant of the invention with a haploid genetic complement of the same or a different variety. In another aspect, the present invention provides a sorghum plant regenerated from a tissue culture that comprises a hybrid genetic complement of this invention.

In still yet another aspect, the present invention provides a method of producing an inbred sorghum plant derived from the sorghum variety GSV644454, the method comprising the steps of: (a) preparing a progeny plant derived from sorghum variety GSV644454, wherein said preparing comprises crossing a plant of the sorghum variety GSV644454 with a second sorghum plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and (d) repeating the steps for an additional 3-10 generations to produce an inbred sorghum plant derived from the sorghum variety GSV644454. In the method, it may be desirable to select particular plants resulting from step (c) for continued crossing according to steps (b) and (c). By selecting plants having one or more desirable traits, an inbred sorghum plant derived from the sorghum variety GSV644454 is obtained which possesses some of the desirable traits of sorghum variety GSV644454 as well as potentially other selected traits.

DETAILED DESCRIPTION OF THE INVENTION

The following definitions apply to the terms used herein:

The characteristic level of a trait that is presented as a rating is indicated or measured using the following 1 through 9 rating scale: 1 to 2 indicates excellent, 3 to 4 indicates very good, 5 to 6 indicates good, 7 to 8 indicates fair, and 9 indicates poor. This scale is used for all traits unless specifically indicated otherwise.

Agronomic Rating. Agronomic rating is a composite rating where consideration is given to all agronomic characteristics that are in evidence at the location where the rating is made.

Allele. An allele is a variant of a DNA sequence at a given locus.

Alter. The term alter or alteration refers to the utilization of up-regulation, down-regulation, or gene silencing.

Anther Color. Anther color is a description of the color of the anthers on the day they are shedding pollen. The color is generally described as yellow, red, or mottled but other colors and descriptions are possible.

Anthocyanin Presence. Anthocyanin presence will be indicated by purple or red coloration in the stalk and leaves, particularly where damage to tissue has occurred. Anthocyanin presence is indicated as present or not present.

Awns. Awns are bristles arising from a spikelet part. Some lines have a very small awn, called a tip awn. Awn presence is indicated as present or not present.

Backcrossing. Backcrossing is a process in which a breeder repeatedly crosses hybrid progeny back to one of the parents. For example, a first generation hybrid $F_1$ may be crossed with one of the parental genotypes of the $F_1$ hybrid.

Barren Plants. Plants that are barren are those that lack a head with grain or that have only a few seeds.

Bloom 10%. Bloom 10% refers to the number of days from planting to when a line in a nursery row or field has completed 10% of the blooming process.

Bloom 50%. Bloom 50% refers to the number of days from planting to when a line in a nursery row or field has completed 50% of the blooming process.

Bloom 90%. Bloom 90% refers to the number of days from planting to when a line in a nursery row or field has completed 90% of the blooming process.

Cell. Cell, as used herein, includes a plant cell, whether isolated, in tissue culture, or incorporated into a plant or plant part.

Charcoal Rot Resistance. Charcoal rot resistance refers to a visual rating of a variety's resistance to Charcoal Rot disease.

Chinch Bug Resistance. Chinch bug resistance refers to a visual rating of the sorghum plant's ability to grow normally when infested with a large number of chinch bugs.

Color Intensity Score. Color Intensity score is a rating of the intensity and brightness of color for a particular variety.

Days to Flower. Days to flower refers to the predicted number of days, measured from the time of planting, required for flowers of a variety to bloom. Days to flower for the same variety may vary depending on the environment in which it is grown.

Days to Harvest. Days to harvest refers to the predicted number of days, measured from the time of planting, required for a variety to be ready for harvest. Days to harvest for the same variety may vary depending on the environment in which it is grown.

Downy Mildew Resistance. Downy mildew resistance refers to a visual rating of a variety's resistance to races 1, 3, and/or 6 of Downy Mildew, a fungal disease that infects sorghum plants.

Endosperm Color. Endosperm color is described as white or yellow.

Endosperm Texture. Endosperm Texture is described as vitreous, floury, or intermediate.

Elite Sorghum Hybrid. An elite sorghum hybrid is a sorghum hybrid which has been sold commercially.

Elite Sorghum Parent Line. An elite sorghum line is a sorghum line which is the parent line of a sorghum hybrid which has been sold commercially.

Embryo. The embryo is the small plant contained within a mature seed.

Essentially all of the physiological and morphological characteristics. This phrase refers to a plant having essentially all of the physiological and morphological characteristics of the referenced plant or variety, as determined at a 5% significance level for quantitative data.

*Fusarium* Head Blight Resistance*. *Fusarium* Head Blight Resistance refers to a visual rating of a variety's resistance to *Fusarium* Head Blight disease, which is caused by *Fusarium moniliforme* Sheld.

Gene. As used herein, gene refers to a segment of nucleic acid. A gene can be introduced into a genome of a species, whether from a different species or from the same species, using transformation or various breeding methods.

Genetic Complement. The phrase genetic complement is used to refer to the aggregate of nucleotide sequences, the expression of which sequences defines the phenotype of a plant, or a cell or tissue of that plant.

Gene Silencing. Gene silencing means the interruption or suppression of the expression of a gene at the level of transcription or translation.

Genotype. Genotype refers to the genetic constitution of a cell or organism.

Glume Color. The glume refers to one of a pair of empty scales at the base of a spikelet. Glume color is described as tan, mahogany, red, purple, or black.

Grain Set Under Bags. Grain set under bags is a measure of the self fertility of a plant. Pollinating bags are placed over the panicle prior to the initiation of flowering and remain in place until seed set can be determined, generally three weeks or more after flowering has been completed. At that time a percentage rating of seed set is made. This can range from 0% (indicating the plant is pollen sterile) to 100% (indicating full pollen fertility). Intermediate ratings can indicate varying levels of partial fertility.

Grain Weathering Resistance. Grain weathering resistance refers to a visual rating of how well the exposed grains in the sorghum head are able to retain normal seed quality when exposed to normal weather hazards and surface molds.

Greenbug Resistance. Greenbug resistance refers to a visual rating of a varieties resistance to one or more biotypes of the greenbug insect pest. Resistance to a particular biotype is indicated by "E" (Biotype E) and/or "I" (Biotype I).

Head Smut Resistance. Head smut resistance refers to a visual rating of a variety's resistance to this fungal disease that infects sorghum plants. The rating is based on the percentage of smut-infected plants.

Height Uniformity. Height uniformity is a rating of the uniformity of the height of all of the main heads and tillers for a variety.

Leaf Attitude. Leaf attitude refers to an indicator of the attitude of the leaves with reference to the stalk, where "E" indicates erect (leaf angle [panicle to leaf axil to leaf midrib] less than about 45 degrees), "SE" indicates semi-erect (leaf angle of about 45-80 degrees), and "H" indicates horizontal (leaf angle of about 80 degrees or greater).

Leaf Color Intensity. The leaf color intensity is described as the color intensity from very light to very dark.

Leaf Length and Width. Leaf length and width is measured by selecting the largest leaf, after flowering, on a representative sample of plants and measuring the maximum length and width in inches. Generally, this will be a leaf towards the middle of the plant.

Leaf Number. Leaf number is measured by counting the total number of leaves on the plant after flowering. Some of the first leaves may have deteriorated by that time, so an estimate can be made.

Locus. A locus is the specific location of a gene or DNA sequence on a chromosome.

Maturity. The maturity of a variety is measured as the number of days between planting and physiological maturity.

Maize Dwarf Mosaic Virus (MDMV). MDMV refers to a visual rating of a variety's resistance to the Maize Dwarf Mosaic Virus, type "A."

Mid-Rib Color. Mid-rib color can be described as white, cloudy, intermediate, or brown. White indicates a dry mid-rib and stalk, while cloudy indicates that they are juicy. Brown indicates the presence of a mutant allele that conditions for a reduced amount of lignin in the plant.

Panicle Appearance Rating. Panicle Appearance Rating is a rating of the overall panicle appearance that includes panicle type, panicle length, panicle diameter, grain color, grain color intensity, grain weathering, seed size, glume size, presence or absence of panicle diseases (i.e. *fusarium* head blight), and other criteria that may be important for a given environment.

Panicle Branch Attitude. Panicle branch attitude is an indicator of the attitude of the panicle branch with reference to the stalk, where "E" indicates erect (panicle branch angle [central rachis to panicle branch axil to panicle branch] less than about 45 degrees), "SE" indicates semi-erect (panicle branch angle of about 45-80 degrees), and "H" indicates horizontal (panicle branch angle of about 80 degrees or greater).

Panicle Blasting Percent. Panicle blasting percent is the percentage of florets in a panicle aborted by a sorghum plant. This data is usually recorded on cytoplasmic male sterile lines and is influenced by genotype and environment. Presence of this condition is a deleterious trait for commercial seed production.

Panicle Branch Length. Panicle Branch Length is measured by selecting panicle branches from the middle of the panicle, which are generally the longest, and measuring the length in inches.

Panicle Diameter. Panicle Branch Diameter is a measurement, in inches, of the largest part of the panicle at the stage when grain is fully mature.

Panicle (or Head) Exsertion. Panicle (or Head) Exsertion is a 1 to 9 rating representing the length of the peduncle exposed between the base of the panicle (head) and the flag leaf of the plant. A high score indicates more distance between the flag leaf and the sorghum head, while a low score indicates a short distance between the two.

Panicle Length. Panicle length is the length of the panicle, in inches, from the attachment point of the lowest branch to the tip of the uppermost branch in its normal orientation.

Panicle (or Head) Type. Panicle (or Head) Type is an indicator of the morphology of a sorghum plant's head (panicle), where "0" indicates an open panicle characterized by either more distance between the panicle branches or longer panicle branches; "SO" indicates a less open panicle; "SC" indicates a semi-compact panicle caused by shorter panicle branches arranged more closely on the central rachis; and "C" indicates a very compact panicle caused by very short panicle branches arranged tightly on the central rachis.

Panicle Shape. Panicle shape is an indicator of the shape of a sorghum plant's head (panicle), where "C" indicates cylindrical, "E" indicates elliptical, "0" indicates oval, and "R" indicates round.

Plant. As used herein, the term plant includes reference to an immature or mature whole plant, including a plant from which seed or grain or anthers have been removed.

Plant Color. Plant color results from the presence or absence of anthocyanin pigments in the stalks and other organs of sorghum plants. The type and degree of coloration is determined by genotype and is somewhat subject to growing conditions, but varieties typically show varying degrees of coloration ranging from: absent (tan plant) to very strong (deep purple coloration). Ratings generally are tan, red, or purple.

Plant Height. Plant height refers to the average height of the plant at the end of flowering, assuming the plant is not lodged. This varies from variety to variety and although it can be influenced by environment, relative comparisons between varieties grown side by side are useful for variety identification. Plant height is measured in inches, from the ground to the tip of the panicle.

Plant Parts. As used herein, the term plant parts (or "sorghum plant, or a part thereof") includes, but is not limited to, protoplasts, leaves, stalks, roots, root tips, anthers, stigmas, panicles, seeds, grains, embryos, pollen, ovules, flowers, shoots, tissue, cells, and meristematic cells.

Pollen Shed Rating. Pollen shed rating is a visual rating made during flowering indicating the amount of pollen shed, on a scale of 1 to 9, where 1 indicates heavy pollen shed and 9 indicates no pollen shed.

Pre-Flower Stress Tolerance. Pre-flower stress tolerance is a visual rating of the stress tolerance of a sorghum plant before flowering. Symptoms that indicate poor pre-flower stress tolerance include poor panicle exertion, delayed panicle development, panicle exsertion, and flowering, and in extreme cases, abortion of the panicle.

Post-Flower Stress Tolerance. Post-flower stress tolerance is a rating of the stress tolerance of a sorghum plant after flowering. Symptoms that indicate poor post-flower stress tolerance include varying degrees of senescence of leaves starting with the lower leaves, pre-disposition and infection by stalk rot organisms such as Charcoal Rot (*Macrophomina phaseolina*), and varying degrees of stalk lodging.

Post-Freeze Standability. Post-freeze standability is a rating of the standability of a sorghum plant after a freeze.

Regeneration. Regeneration refers to the development of a plant from tissue culture.

Relative Maturity. Relative maturity (RM) for a variety is based on the predicted number of days required for an inbred line or hybrid to reach the blooming stage from the time of planting. The RM rating is relative to a set of known check varieties and is determined using standard linear regression analysis.

Resistance to Lodging. Resistance to lodging is a visual rating (relative to check varieties) of a variety's ability to stand up in the field under high yield conditions and severe environmental factors. A variety can have good (remains upright), fair, or poor (falls over) resistance to lodging. The degree of resistance to lodging is not expressed under all conditions but is most meaningful when there is some degree of lodging in a field trial.

Root Lodging. Root lodging is the percentage of lodged plants of a variety caused by an inadequate root support system. If the stem of the plant leans at an angle of approximately 30 degrees or more from vertical, the plant is considered to be root lodged.

Seed Coat Color. The color of the seed coat can be variety-specific and can be red, brown, white, or yellow for inbred lines. For hybrids, the seed coat color may also be cream (from a white×yellow cross) and bronze (from a red×yellow cross).

Seeds per Pound. Seeds per pound refers to the number of seeds per pound of grain for a representative sample.

Seedling Vigor. Seedling vigor is a visual rating of the amount of vegetative growth. The rating is usually taken when the average entry in the trial is at the two- to three-leaf stage.

Selection Index. The selection index provides a single measure of a variety's performance based on a composite of multiple traits. A sorghum breeder may utilize his or her own set of traits for the selection index. Two of the traits usually included are yield and days to flower (relative maturity). The selection index data presented herein represent the mean values averaged across testing locations.

Single Gene Converted (Conversion). Single gene conversion or a single gene converted plant refers to plants that are developed by backcrossing, genetic engineering, or mutation, wherein essentially all of the physiological and morphological characteristics of a variety are recovered, in addition to the single gene transferred into the variety via the backcrossing technique, genetic engineering, or mutation.

Sorghum Midge Resistance. Sorghum Midge Resistance refers to a visual rating of a variety's resistance to sorghum midge, an insect pest that affects seed set by infecting the head.

Stalk Lodging. Stalk lodging refers to the percentage of lodged plants of a variety caused by stalks breaking above the ground due to natural causes.

Staygreen. Staygreen refers to a visual rating of a variety's ability to retain green leaf tissue. Ratings are most valuable in the presence of heat and/or drought stress during the grain fill period.

Testweight. Testweight is a measure of the weight (in pounds) of the grain harvested from a variety for a given volume (bushel), adjusted to a standard grain moisture content.

Threshability. Threshability refers to a visual rating (relative to check varieties) of the tendency of the seed of a variety to thresh free from the glumes.

Tillering. Tillering is a measure of the development of shoots from buds at the base of the main stem. This can be expressed as a visual rating (on a scale of 1 to 9, with 1 being a high degree of tillering and 9 being no tillering. This can also be expressed as an actual number of tillers per plant.

Tissue Culture. Tissue culture encompasses all cultural techniques in which a composition comprising embryonic issues, tissue fragments, calli, isolated cells or protoplasts of the same or a different type, or a collection of such cells are organized into a culture for the regeneration of functional plants or plant parts.

Yield. This term refers to the actual yield (measured in pounds per acre) of the grain harvested from a unit area for a variety, adjusted to a standard 13% grain moisture content.

Yield Under Stress. Yield under stress is a rating of the yield of grain harvested from a unit area when such unit area is under stress, for example, from drought or heat. This can be determined by comparing the points where regression lines intersect the y axis for different hybrids when yield for the individual hybrids is regressed against the average yield for all hybrids in the tests. A high value for y axis intercept indicates a drought and stress tolerant hybrid whereas a low value indicates poor drought and stress tolerance.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Sorghum plants (*Sorghum bicolor* (L.) Moench) have both male (anthers) and female (stigma) reproductive parts located in the same flower in the panicle. Natural pollination occurs in sorghum when anthers shed pollen and pollen falls onto receptive *stigmata*. Because of the close proximity of the anthers and *stigmata* in the panicle, the rate of self-pollination is very high (average 94%).

In an embodiment, the present invention relates to a sorghum plant of the variety designated GSV644454. The inbred sorghum plant variety designated GSV644454 was derived from an initial cross between the lines 602 and ((629GBx348PI)3-12(YZ55)x602)BI. The origin and breeding history of the sorghum variety designated GSV644454 can be summarized as follows:

Winter 1999 at Santa Isabel, Puerto Rico. The inbred line 602 B (a proprietary Monsanto Company inbred) was crossed to the inbred line ((629GBx348PI)3-12(YZ55)x602) BI B (a proprietary Monsanto Company inbred) using a wet pollen emasculation between nursery rows PR976 and PR984 in Nursery PR to produce an $F_1$.

Summer 2000 at Bishop, Tex. The $F_1$ was grown and self-pollinated using open pollination in Nursery BI Row 83 to produce $F_2$ seed. The line was then coded to (602x(629 GBx348PI)3-12(YZ55))xBC2)BI.

Summer 2001 at Bishop, Tex. The $F_2$ was grown in Nursery $F_2$ Row 1127. It was self-pollinated and $F_3$ selection was harvested. In this and in subsequent selection opportunities yield, stalk quality, root quality, disease tolerance, pollen shedding ability, insect tolerance, plant height, head exsertion, and stress tolerance were some of the criteria used to determine which plants were selected.

Summer 2002 at Bishop, Tex. The $F_3$ was grown in Nursery $F_3$ Row 1519. It was self-pollinated and $F_4$ selection was harvested.

Summer 2003 at Plainview, Tex. The $F_4$ was grown in Nursery F Row 2283. It was self-pollinated and the $F_5$ selection was harvested. The MSC0 generation of the A Line was also produced in this nursery by collecting pollen from this nursery row and using it to pollinate bagged sterile heads of 174 A in Nursery F Row 2273. At this point the component lines were coded. 602 was coded to 14 and (629gbx348PI)3-12(YZ55) was coded to 82.

Summer 2004 at Lubbock, Tex. The MSC0 and $F_5$ A/B pair was grown in Nursery A Rows 2984 and 2983 respectively. Sterile heads in the MSC0 Line were pollinated by the $F_5$ B Line to produce MSC1 seed. The B Line was self-pollinated using pollinating bags and the $F_6$ selection was harvested.

Summer 2005 in Plainview, Tex. The MSC1 and $F_6$ A/B pair was grown in Nursery B Rows 6448 and 6447 respectively. Sterile heads in the MSC1 Line were pollinated by the $F_6$ B Line to produce MSC2 seed. The B Line was self-pollinated using pollinating bags and the $F_7$ selection was harvested. The B line was finished at that point with a pedigree of GSV644454.

Summer 2006 at Plainview, Tex. The MSC2 and $F_7$ A/B pair was grown in Nursery D Range 9 Columns 49 and 50, respectively. Sterile heads in the MSC2 Line were pollinated by the $F_7$ B Line to produce MSC3 seed. The B Line was self-pollinated using pollinating bags and the $F_8$ selection was harvested.

Summer 2007 at Bishop, Tex. The MSC3 and $F_8$ A/B pair was grown in Nursery Block 7 Range 714 Column 40 respectively. Sterile heads in the MSC3 Line were pollinated by the $F_8$ B Line to produce MSC4 seed. The B Line was self-pollinated using pollinating bags and the $F_9$ selection was harvested.

Winter 2007 at San Juan de Abajo, Mexico. The MSC4 and $F_9$ A/B pair was grown in Nursery SJA Range 4 Column 55 and 56 respectively. Sterile heads in the MSC4 Line were pollinated by the $F_9$ B Line to produce MSC5 seed. The B Line was self-pollinated using pollinating bags and the $F_{10}$ selection was harvested.

Summer 2008 at Bishop, Tex. The MSC5 and $F_{10}$ A/B pair was grown in Nursery Block 7 Range 709 Columns 3 and 4 respectively. Sterile heads in the MSC5 line were pollinated by the $F_{10}$ line to produce MSC6 seed. The B line was self-pollinated using pollinating bags and the $F_{11}$ selection was harvested.

Winter 2008 at San Juan de Abajo, Mexico. A MSC6 derived bulk was grown in Nursery SJA2 Range 17 Column 29. It was bagged and crossed by an $F_{11}$ derived bulk of the B Line and sufficient bulk seed of the A Line was generated (an MSC6 derived bulk in the MSC7) to plant a seedstock increase and a pilot hybrid production block at Dumas, Tex. in Summer 2009. An $F_{11}$ derived bulk was grown in Nursery SJA2 Range 31 Column 33. It was self-pollinated using pollinating bags and sufficient bulk seed was generated (an $F_{11}$ derived bulk in the $F_{12}$) to plant a seedstock increase block at Dumas, Tex. in Summer 2009.

In an embodiment, the invention relates to sorghum plants having all or essentially all of the physiological and morphological characteristics of the inbred sorghum variety GSV644454. In an embodiment, the physiological and morphological characteristics of the inbred sorghum variety are set forth in Table 1. Sorghum variety GSV644454 has shown acceptable levels of uniformity and stability, within the limits of environmental influence, for the traits described in Table 1. Sorghum variety GSV644454 has been self-pollinated and head-rowed a sufficient number of generations to ensure homozygosity and phenotypic stability. In certain categories of variety description information, GSV644454 has been compared to sorghum varieties TX2737 and OK11.

TABLE 1

Physiological and Morphological Characteristics for Sorghum Variety GSV644454 and Comparative Check Varieties

| | CHARACTERISTIC | VALUE** | | |
| --- | --- | --- | --- | --- |
| | | GSV644454 | TX2737 | OK11 |
| 1.A. | STALK | | | |
| | Plant Height (in.) | 45.2 | 51.3 | 43.7 |
| | Head Exsertion (rating) | 3.6 | 4.7 | 3.7 |
| | Anthocyanin Presence | Yes | Yes | Yes |
| | Tillering (rating) | 4.8 | 5.7 | 5.0 |
| 1.B. | LEAF | | | |
| | Color | Medium | Medium Dark | Medium Light |
| | Length (in.) | 23.1 | 25.0 | 24.5 |
| | Width (in.) | 2.8 | 2.5 | 3.0 |
| | No. per Stalk. | 13 | 11 | 12 |
| | Mid Rib Color (e.g. cloudy) | Cloudy | Cloudy | Cloudy |
| | Color Pattern (e.g. solid) | Solid | Solid | Solid |
| | Attitude | SE | E | SE |
| 1.C. | HEAD | | | |
| | Panicle Type | SC | SC | SO |
| | Panicle Shape | C | C | E |
| | Panicle Length (in.) | 9.4 | 12.5 | 12.0 |
| | Panicle Branch Attitude | E | E | SE |
| | Panicle Branch Length (in.) | 4.2 | 2.25 | 3.0 |
| | Grain Set Under Bags | 0% | >95% | 0%* |
| | Panicle Blasting Percent | 2% | 0% | 3%* |
| | Pollen Shed (rating) | 9.0 | 2.7 | 9.0* |
| 1.D. | GRAIN | | | |
| | Glume Color | Mahogany | Tan | Purple |
| | Awns (e.g. present or absent) | Present | Absent | Absent |
| | Seeds per Pound | 20,136 | 15,564 | 12,720 |
| | Grain Color | Red | Yellow | White |
| | Test Weight (lbs per bu) | 56.8 | 60.1 | 59.1 |
| | Endosperm Color | White | White | White |
| | Endosperm Texture | Intermediate | Vitreous | Intermediate |
| | Threshability (rating) | 2 | 2 | 3 |
| | Grain Weathering Resistance (rating) | 3 | 4 | 4 |
| 1.E. | DISEASE TOLERANCE | | | |
| | Downy Mildew-pathotype 1 (rating) | 9.0 | 9.0 | 9.0 |
| | Downy Mildew-pathotype 3 (rating) | 9.0 | 9.0 | 9.0 |
| | Downy Mildew-pathotype 6 (rating) | 9.0 | 9.0 | 9.0 |
| | Maize Dwarf Mosaic Virus "A" (rating) | na | na | na |
| | Head Smut-Race 1 (rating) | 3.0 | 4.0 | 5.0 |
| | Charcoal Rot (rating) | 3.0 | 3.0 | 2.0 |
| | *Fusarium* Head Blight (rating) | 4.0 | 4.0 | 6.0 |
| 1.F. | INSECT RESISTANCE | | | |
| | Greenbug Biotype E (rating) | na | na | na |
| | Greenbug Biotype I (rating) | na | na | na |
| | Chinch Bug (rating) | na | na | na |
| | Sorghum Midge (rating) | 9.0 | 9.0 | 9.0 |
| 1.G. | PLANT GROWTH | | | |
| | Seedling Vigor (rating) | 2.5 | 5.0 | 6.3 |
| | Plant Color | Purple | Purple | Purple |
| | Staygreen (rating) | 3.0 | 3.0 | 2.0 |
| | Height Uniformity (rating) | 1.5 | 3.3 | 2.7 |
| | Root Lodging (rating) | 2.0 | 3.0 | 3.0 |
| | Pre-Flower Stress Tolerance (rating) | 3.0 | 2.0 | 3.0 |
| | Post-Flower Stress Tolerance (rating) | 3.0 | 3.0 | 2.0 |
| | Post-Freeze Standability (rating) | 3.0 | 3.0 | 3.0 |
| | Yield Under Stress (rating) | 3.0 | 2.0 | 3.0 |
| | Chemical Burn Resistance (rating) | na | na | na |
| | Bloom 10% | 75 | 70.8 | 82.0 |

TABLE 1-continued

Physiological and Morphological Characteristics for Sorghum Variety GSV644454 and Comparative Check Varieties

| CHARACTERISTIC | VALUE** | | |
|---|---|---|---|
| | GSV644454 | TX2737 | OK11 |
| Bloom 50% | 76 | 73.7 | 84.2 |
| Bloom 90% | 80 | 76.5 | 86.8 |
| Agronomic Rating | 3.8 | 2.8 | 3.3 |

**These are typical values. Values may vary due to environment.

In an embodiment, the sorghum plants of the invention are inbred. Inbred GSV644454 sorghum plants can be produced by planting the seeds of the inbred sorghum plant designated GSV644454 and growing the resulting sorghum plants under self-pollinating or sib-pollinating conditions with adequate isolation, using standard techniques well known to an artisan skilled in the agricultural arts.

In a particular embodiment, the present invention provides a method of producing an inbred sorghum plant derived from the sorghum variety designated GSV644454, the method comprising the steps of: (a) preparing a progeny plant derived from sorghum variety GSV644454, wherein said preparing comprises crossing a plant of the sorghum variety GSV644454 with a second sorghum plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and (d) repeating the steps for an additional 3 to 10 generations to produce an inbred sorghum plant derived from the sorghum variety GSV644454. In the method, it may be desirable to select particular plants resulting from step (c) for continued crossing according to steps (b) and (c). By selecting plants having one or more desirable traits, an inbred sorghum plant derived from the sorghum variety GSV644454 may be obtained which possesses some or essentially all of the desirable traits of sorghum variety GSV644454 as well as potentially other selected traits. In a particular embodiment, the invention comprises an elite GSV644454 sorghum parent plant or line.

In yet another embodiment, the invention is directed to parts of a sorghum plant of variety GSV644454. Any part of the GSV644454 sorghum plant is contemplated in this embodiment. In an embodiment, the plant part may comprise pollen obtained from a sorghum plant of variety GSV644454. In still another embodiment, the invention comprises seed of the GSV644454 sorghum plant. Seeds can be harvested from a GSV644454 plant using standard, well-known procedures.

In an embodiment, the seeds are inbred GSV644454 seeds. Inbred sorghum seed of the invention may be provided as an essentially homogeneous population of inbred sorghum seed of the variety designated GSV644454. Essentially homogeneous populations of inbred seed may be free from substantial numbers of seeds that are significantly different on a genetic basis. In an embodiment of the present invention, inbred seed may form greater than about 97% of the total seed. In an embodiment, the population of inbred sorghum seed of the invention may be essentially free from hybrid seed. In some embodiments, the inbred seed population may be grown separately from any hybrid population to provide an essentially homogeneous population of inbred sorghum plants designated GSV644454.

In yet another embodiment of the invention, a tissue culture of regenerable cells of a plant of the variety designated GSV644454 is provided. The regenerable cells in such tissue cultures may be derived from embryos, meristematic cells, microspores, pollen, anthers, stigma, flowers, leaves, stalks, roots, root tips, seeds, or from callus or protoplasts derived from those tissues. Means for preparing and maintaining plant tissue cultures are well known in the art.

In an embodiment, the tissue culture may be capable of regenerating plants capable of expressing all of the physiological and morphological characteristics of the GSV644454 variety, and of regenerating plants having substantially the same genotype as other plants of the GSV644454 variety. Still further, the present invention provides sorghum plants regenerated from the tissue cultures of the invention, the plants having all of the physiological and morphological characteristics of the variety designated GSV644454.

In a particular embodiment, the invention relates to a sorghum hybrid containing the sorghum variety GSV644454. A sorghum hybrid is the cross of two inbred lines, each of which may have one or more desirable characteristics lacked by the other and/or which complement the other. As used herein, crossing can include selfing, backcrossing, crossing to another or the same inbred, crossing to populations, and the like.

In an embodiment, the sorghum plants can be crossed by either natural or mechanical techniques. Natural pollination occurs in sorghum when wind blows pollen from the anthers to receptive *stigmata* on the same or another plant. Mechanical pollination can be effected either by controlling the types of pollen that can blow onto the receptive *stigmata* or by pollinating by hand. These techniques are well known in the art.

Because sorghum is normally a self-pollinated plant and because both male and female flowers are in the same panicle, a cytoplasmic male sterile (CMS) inbred may be used to produce large quantities of hybrid seed. Cytoplasmic-male sterility is a pollen abortion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus, and will continue to be male sterile in the next generation. The male fertility of a CMS plant can be restored in the subsequent generation by crossing it with a plant that contains the restorer gene(s) in the nucleus. With the restorer gene(s) in the nucleus, the offspring of the male-sterile plant can produce normal pollen grains and propagate. Thus, in a hybrid seed production system, flowers of a CMS inbred (non-restorer female parent) may be fertilized with pollen from a fertile inbred (restorer male parent) carrying genes which restore male fertility in the hybrid ($F_1$) progeny.

The development of a sorghum hybrid, in an embodiment, may involve the following steps: (1) the formation of "restorer" and "non-restorer" germplasm pools; (2) the selection of superior plants from various "restorer" and "non-restorer" germplasm pools; (3) the selfing of the superior plants for one or more generations to produce a series of inbred lines, which although different from each other, breed true and are highly uniform; (4) the conversion of inbred lines classified as females or non-restorers to CMS forms; and (5) crossing the selected CMS female inbred lines with selected fertile male inbred lines to produce the hybrid progeny ($F_1$).

In another embodiment, the development of a sorghum hybrid may involve the steps of: (1) planting in pollinating proximity seeds of a first and second parent sorghum plant (the first and second plant may be distinct inbred plants); (2) cultivating or growing the seeds of the first and second parent sorghum plants into plants that bear flowers; (3) emasculating the flowers of either the first or second parent sorghum plant, i.e. physically removing the anthers from the florets prior to blooming of the flowers so as to prevent pollen production or preventing dehiscence of pollen from anthers by introduction and maintenance of a high humidity environment by bagging a panicle or portion of a panicle with a plastic bag prior to blooming (a "wet pollination emasculation") or by using as the female parent a male sterile plant, thereby providing an emasculated parent sorghum plant; (4) allowing natural cross-pollination to occur between the first and second parent sorghum plants or mechanically moving pollen from the pollen parent to the pollen sterile seed parent; (5) harvesting seeds produced on the emasculated parent sorghum plant; and, where desired, (6) growing the harvested seed into a sorghum plant, which may be a hybrid sorghum plant.

In one embodiment, the sorghum hybrid containing the variety GSV644454 is a single cross hybrid. A single cross sorghum hybrid is the cross of two inbred plants, each of which has a genotype that complements the genotype of the other. In this embodiment, the $F_1$ hybrid may be more vigorous than its inbred parents. This hybrid vigor, or heterosis, may be manifested in many polygenic traits, including markedly improved yields, better stalks, better roots, better uniformity and better insect and disease resistance.

In an embodiment of the invention, either the first or second parent sorghum plants can be from variety GSV644454. Thus, any sorghum plant produced using sorghum plant GSV644454 forms a part of the invention. In an embodiment, the parent sorghum plants may be of different varieties. In still another embodiment, the invention comprises an elite hybrid containing the GSV644454 sorghum plant or line.

Sorghum lines are known to those of skill in the art, any one of which could be crossed with sorghum plant GSV644454 to produce a hybrid plant. An example of an $F_1$ hybrid which has been produced with GSV644454 as a parent is the hybrid sorghum variety designated Hybrid 1. An objective description of this hybrid is presented in Table 2 below.

TABLE 2

Physiological and Morphological Characteristics of a Sorghum Hybrid Having Sorghum Variety GSV644454 as One Parent

| CHARACTERISTIC | | VALUE |
|---|---|---|
| 1. | STALK | |
| | Plant Height (in.) | 50.1 |
| | Tillering (rating) | 2 |
| | Head Exsertion (rating) | 5 |
| | Plant Color | Purple |
| 2. | LEAF | |
| | Length (in.) | 23.5 |
| | Width (in.) | 2.8 |
| | Midrib Color | Cloudy |
| | Leaf Attitude | Slightly Erect |
| 3. | PANICLE | |
| | Length (in.) | 10.3 |
| | Panicle Branch Length (in.) | 3.6 |
| | Anther Color | Yellow |
| | Glume Color | Tan |
| | Panicle Type | SO |
| | Panicle Diameter (in.) | 2.7 |
| | Awns (present or absent) | Absent |
| | Panicle Appearance (rating) | 5.0 |
| 4. | GRAIN | |
| | Endosperm Texture | Intermediate |
| | Endosperm Color | White |
| | Grain Color | Bronze |
| | Color Intensity (rating) | 5.0 |
| | Seeds Per Pound | 21,500 |

Examples of comparative data for Sorghum Hybrid 1 are set forth in Table 3, which presents a comparison of performance data for a hybrid made with GSV644454 as one parent, versus selected commercial hybrids. All the data in Table 3 represents results across years and locations for research and/or strip trials.

TABLE 3

Comparative Data for Sorghum Hybrid 1, a Hybrid Having GSV644454 as One Inbred Parent

| HYBRID | YLD | MST | STL | RTL | BLM | AGR | PHT | TWT | THR |
|---|---|---|---|---|---|---|---|---|---|
| Hybrid 1 | 4,678 | 13.1 | 1 | 2 | 59 | 3.9 | 50 | 60.0 | 4.0 |
| Asgrow Pulsar | 4,520 | 13.1 | 1 | 3 | 59 | 4.6 | 48 | 58.9 | 3.0 |
| Differential | 158 | 0.0 | 0 | −1 | 0 | −0.7 | 2 | 1.1 | 1.0 |
| Significance Level | NS | NS | NS | NS | NS | ** | * | ** | NS |
| Hybrid 1 | 5,738 | 14.2 | 2 | 1 | 57 | 4.3 | 49 | 59.9 | 4.0 |
| Channel 6B13 | 5,717 | 14.6 | 3 | 1 | 59 | 4.6 | 51 | 59.8 | 1.0 |
| Differential | 21 | −0.4 | −1 | 0 | −2 | −0.3 | −2 | 0.1 | 3.0 |
| Significance Level. | NS | * | NS | NS | + | NS | + | NS | NS |
| Hybrid 1 | 5,738 | 14.2 | 2 | 1 | 57 | 4.3 | 49 | 59.9 | 4.0 |

TABLE 3-continued

Comparative Data for Sorghum Hybrid 1, a Hybrid Having GSV644454 as One Inbred Parent

| HYBRID | YLD | MST | STL | RTL | BLM | AGR | PHT | TWT | THR |
|---|---|---|---|---|---|---|---|---|---|
| Fontanelle W-4525 | 5,100 | 13.7 | 1 | 1 | 59 | 3.6 | 46 | 58.2 | 3.0 |
| Differential | 638 | 0.5 | 1 | 0 | −2 | 0.7 | 3 | 1.8 | 1.0 |
| Significance Level | ** | * | NS | NS | + | ** | ** | ** | NS |

Significance levels are indicated as: + = 10%, * = 5%, ** = 1%
Rating Scale: 1 = excellent; 9 = poor.

ABBREVIATIONS LEGEND

| Abbreviation | Meaning |
|---|---|
| AGR | Agronomic Rating |
| BLM | Bloom 50% |
| FNSC | Final Stand Count (actual count) |
| GSB | Grain Set under Bags |
| MST | Moisture at harvest (%) |
| na | Not Available |
| NS | Not Significant |
| PHT | Plant Height (inches) |
| PSR | Pollen Shed Rating |
| UNI | Plant Uniformity Rating |
| RTL | Root Lodging (%) |
| SGR | Staygreen Rating |
| SI | Selection Index (% of check) |
| STL | Stock Lodging (%) |
| SVR | Seedling Vigor Rating |
| THR | Threshability Rating |
| TWT | Test Weight (pounds) |
| YLD | Yield (bushels/acre) |

Another aspect of the invention is a sorghum plant of sorghum variety GSV644454 further comprising a single locus conversion. In one embodiment, the sorghum plant is defined as comprising the single locus conversion and otherwise capable of expressing all of the physiological and morphological characteristics of the sorghum variety GSV644454. In another embodiment of the invention, a plant of sorghum variety designated GSV644454 comprising an added heritable trait is provided. The heritable trait may comprise a genetic locus that is a dominant or recessive allele. When introduced through transformation, a genetic locus may comprise one or more transgenes integrated at a single chromosomal location. In specific embodiments of the invention, an added genetic locus confers one or more additional traits. The traits conferred may include, but are not limited to, male sterility, male fertility, herbicide tolerance or resistance, insect tolerance or resistance, disease tolerance or resistance, fungal tolerance or resistance, waxy starch, enhanced nutritional quality, modified phytic acid metabolism, modified carbohydrate metabolism and modified protein metabolism.

In an embodiment, the trait may be cytoplasmically-inherited and may be passed to progeny through the female parent in a particular cross. An exemplary cytoplasmically-inherited trait is the male sterility trait. A cytoplasmically-inherited trait may be a naturally-occurring sorghum trait or a trait introduced through genetic transformation techniques.

In other embodiments, the trait may be conferred by a naturally-occurring sorghum gene introduced into the genome of the variety designated GSV644454 by backcrossing, a natural or induced mutation, or a transgene introduced through genetic transformation techniques. If backcrossing is used in an embodiment, essentially all of the physiological and morphological characteristics of a variety may be recovered in addition to a genetic locus transferred into the plant via the backcrossing technique.

In a backcross procedure, the parental sorghum plant which contributes the locus or loci for the desired trait is typically termed the non-recurrent or donor parent. This terminology refers to the fact that the non-recurrent parent is used one time in the backcross protocol and, therefore, does not reoccur.

The parental sorghum plant to which the locus or loci from the non-recurrent parent are transferred is known as the recurrent parent, as it is used for several rounds in the backcrossing protocol. In a typical backcross protocol, the original parent of interest (recurrent parent) is crossed to a second variety (non-recurrent parent) that carries the genetic locus of interest to be transferred. The resulting progeny from this cross are then crossed again to the recurrent parent and the process is repeated until a sorghum plant is obtained wherein essentially all of the desired physiological and morphological characteristics of the recurrent parent are recovered in the converted plant, in addition to the transferred locus from the non-recurrent parent. The backcross process may be accelerated by the use of genetic markers, such as single sequence repeat (SSR), restriction fragment length polymorphism (RFLP), single nucleotide polymorphism (SNP) or amplified fragment length polymorphism (AFLP) markers to identify plants with the greatest genetic complement from the recurrent parent.

The selection of a suitable recurrent parent is an important step for a successful backcrossing procedure. The choice of the particular non-recurrent parent will depend on the purpose of the backcross. One of the major purposes is to add commercially desirable, agronomically important traits to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine which progeny carry the desired allele.

As part of the invention, direct selection may be applied where a genetic locus acts as a dominant trait. An example of a dominant trait may be a herbicide resistance trait, which, in some cases, is inherited in a dominant fashion. For this selection process, the progeny of the initial cross may be sprayed with the herbicide prior to the backcrossing. The spraying eliminates any plants which do not have the desired herbicide resistance characteristic, and only those plants that have the herbicide resistance gene are used in the subsequent backcross. This process is then repeated for all additional backcross generations.

It will be understood by those of skill in the art that a transgene need not be directly transformed into a GSV644454 plant, as techniques for the production of stably transformed sorghum plants that pass single loci to progeny by Mendelian inheritance are known in the art. Such loci may, therefore, be passed from parent plant to progeny plants by standard plant breeding techniques that are well known in the art. Examples of traits that may be introduced into a sorghum plant of variety GSV644454 according to the invention are provided herein below.

Methods for transformation of sorghum plants are well known in the art. Included among the various known plant transformation techniques are methods that permit the site-specific modification of a plant genome, including coding sequences, regulatory elements, non-coding and other DNA sequences in a plant genome. Such methods are well-known in the art and include, for example, use of the CRISPR-Cas system, zinc-finger nucleases (ZFNs), and transcription activator-like effector nucleases (TALENs), among others.

Plant transformation may involve in one embodiment the construction of an expression vector which will function in plant cells. Such a vector can comprise DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed plants using known transformation methods to incorporate transgenes into the genetic material of the plant(s).

A. Male Sterility

In an embodiment, a male sterility trait is introduced into a sorghum plant. Any gene conferring male sterility may be utilized in this embodiment. In a particular embodiment, the male sterility gene may be herbicide-inducible. Male sterility genes may increase the efficiency with which hybrids are made, in that they eliminate the need to physically emasculate the sorghum plant used as a female in a given cross.

Where the employment of male-sterility systems is desired with a sorghum plant in accordance with the invention, it may be beneficial to also utilize one or more male-fertility restorer genes. For example, where CMS is used, hybrid seed production requires three inbred lines: (1) a CMS female parent line having a CMS cytoplasm and possessing no restorer genes (also known as an "A" line); (2) a fertile inbred with normal cytoplasm that possesses no restorer genes, which is isogenic with the CMS line for nuclear genes (also known as a "maintainer line" or "B line"); and (3) a distinct, fertile, male parent line with normal cytoplasm, carrying fertility restorer genes (also known as the "restorer line" or "R line"). The CMS female parent line is propagated by pollination with the maintainer line, with all of the progeny being male sterile, as the CMS cytoplasm is derived from the female parent. These male sterile plants can then be employed as the female parent in hybrid crosses with the male restorer parent, without the need for physical emasculation of the male reproductive parts of the female parent.

The presence of a male-fertility restorer gene in the male parent results in the production of fully fertile $F_1$ hybrid progeny. If no restorer gene is present in the male parent, male-sterile hybrids are obtained. Such hybrids are useful where the vegetative tissue of the sorghum plant is utilized, e.g., for silage, but in most cases, the seeds will be deemed the most valuable portion of the crop. In these cases, fertility of the hybrids in these crops must be restored. Therefore, one aspect of the current invention concerns plants of the sorghum variety GSV644454 comprising a genetic locus capable of restoring male fertility in an otherwise male-sterile plant. Examples of male-sterility genes and corresponding restorers which could be employed with the plants of the invention are known to those of skill in the art of plant breeding.

B. Herbicide Resistance or Tolerance

In an embodiment, a herbicide resistance or tolerance trait is introduced into a sorghum plant of variety GSV644454. Any gene conferring herbicide resistance or tolerance may be utilized in this embodiment. In an embodiment, the herbicide resistance or tolerance is for imidazolinone herbicides, sulfonylurea herbicides, triazine herbicides, phenoxy herbicides, cyclohexanedione herbicides, benzonitrile herbicides, 4-hydroxyphenylpyruvate dioxygenase-inhibiting herbicides, protoporphyrinogen oxidase-inhibiting herbicides, acetolactate synthase-inhibiting herbicides, 1-aminocyclopropane-1-carboxylic acid-inhibiting herbicides, bromoxynil, nicosulfuron, 2,4-dichlorophenoxyacetic acid (2,4-D), dicamba, quizalofop-p-ethyl, glyphosate, or glufosinate. Numerous herbicide resistance genes are known and may be employed with the invention.

C. Waxy Starch

In an embodiment, a waxy starch trait is introduced into a sorghum plant of variety GSV644454. Any gene conferring waxy starch characteristics may be utilized in this embodiment. The waxy characteristic is an example of a recessive trait. In this example, the progeny resulting from the first backcross generation (BC1) may be grown and selfed. A test may then be run on the selfed seed from the BC1 plant to determine which BC1 plants carried the recessive gene for the waxy trait.

D. Disease Resistance or Tolerance

In an embodiment, a disease resistance or tolerance trait is introduced into a sorghum plant of variety GSV644454. Any gene conferring disease resistance or tolerance may be utilized in this embodiment. In an embodiment, the gene may confer disease resistance to downy mildew, pathotypes 1, 3, or 6; maize dwarf mosaic virus "A"; head smut, race 1; charcoal rot; or *fusarium* head blight. In an embodiment, the disease may be a viral disease.

E. Insect Resistance or Tolerance

In an embodiment, an insect resistance or tolerance trait is introduced into a sorghum plant of GSV644454. Any gene conferring insect resistance or tolerance may be utilized in this embodiment. In an embodiment, such gene may confer resistance to greenbug, biotype C, E, or I; chinch bug; or sorghum midge.

F. Modified Phytate and Carbohydrate Metabolism

In an embodiment, a trait that confers modified phytate or carbohydrate metabolism is introduced into a sorghum plant of GSV644454. Any gene conferring modified phytate or carbohydrate metabolism may be utilized in this embodiment. For example, phytate metabolism may be modified by introduction of a phytase-encoding gene to enhance breakdown of phytate, adding more free phosphate to the transformed plant. A number of genes that may be used to alter carbohydrate metabolism are well known in the art.

G. Origin and Breeding History of an Exemplary Introduced Trait

GSV548413 A is a conversion of GSV548413 to cytoplasmic male sterility. GSV548413 A was derived using backcross methods. GSV548413 (a proprietary inbred of Monsanto Company) was used as the recurrent parent and GSV160919, a germplasm source carrying A1 cytoplasmic sterility, was used as the non-recurrent parent. The breeding history of the converted inbred GSV548413 A can be summarized as follows:

| | |
|---|---|
| Plainview, TX Nurseries 2003 | Made up MSCO: Female row 03 10 41 41 TXPLROY_00047_00029; Male row 03 10 41 41 TXPLROY_00013_00033 |
| Plainview, TX Nurseries 2004 | MSCO was grown and plants selected for recurrent parent type were backcrossed by GSV548413 B (rows 04 05 41 41 TXLUNURA_00039_00077 X 04 05 41 41 TXLUNURA_00039_00078) |
| Plainview, TX Nurseries 2005 | MSC1 was grown and plants selected for recurrent parent type were backcrossed by GSV548413 B (rows 05 05 41 41 TXLUNURA_00023_00092 X 05 05 41 41 TXLUNURA_00023_00093) |
| Mt. Hope, KS Nurseries 2007 | MSC2 was grown and plants selected for recurrent parent type were backcrossed by GSV548413B (rows 07 04 92 92 KSMH3B_00010_00017 X 07 04 92 92 KSMH3B_00010_00018) |
| San Juan de Abajo, MX Nurseries 2007-2008 | MSC3 was grown and plants selected for recurrent parent type were backcrossed by GSV548413B (rows 07 12 92 92 JAPV3_00037_00023 X 07 12 92 92 JAPV3_00037_00024) |
| Mt. Hope, KS Nurseries 2008 | MSC4 was grown and plants selected for recurrent parent type were backcrossed by GSV548413B (rows 08 04 92 92 KSMH4A_00063_00027 X 08 04 92 92 KSMH4A_00063_00028) |
| San Juan de Abajo, MX Nurseries 2008-2009 | MSC5 was grown and plants selected for recurrent parent type were backcrossed by GSV548413B (rows 0812 92 92 JAPV2A_00046_00001 X 08 12 92 92 JAPV2A_00046_00002) |
| Mt. Hope, KS Nurseries 2009 | MSC6 was grown and plants were bulk crossed by GSV548413B to generate approximately one pound of seed (rows 09 04 92 92 KSMH1_00017_00001 X 09 04 92 92 KSMH1_00017_00002) |
| Villa Hidalgo, MX Nurseries 2009-2010 | MSC7 was grown and plants were bulk crossed by GSV548413B to generate approximately 30 pounds of seed for pilot and seedstock production in 2010 (rows 09 12 92 92 JAPVBLK1_00027_00057 to 09 12 92 92 JAPVBLK1_00027_00062 and 09 12 92 92 JAPVBLK1_00028_00037 to 09 12 92 92 JAPVBLK1_00028_00060 in paired rows) |

H. Illustrative Procedures for Introduction of a Desired Trait

As described above, techniques for the production of sorghum plants with added traits are known in the art. An example of such a procedure for preparation of a sorghum plant of GSV644454 comprising an added trait is as follows:

(a) crossing sorghum plant GSV644454 to a second (non-recurrent) sorghum plant comprising a locus to be converted in sorghum plant GSV644454;
(b) selecting at least a first progeny plant resulting from the crossing and comprising the locus;
(c) crossing the selected progeny to sorghum plant GSV644454; and
(d) repeating steps (b) and (c) until a plant of variety GSV644454 is obtained comprising the locus.

Following these steps, essentially any locus may be introduced into sorghum variety GSV644454. For example, molecular techniques allow introduction of any given locus, without the need for phenotypic screening of progeny during the backcrossing steps. Polymerase chain reaction (PCR) and Southern hybridization are two examples of molecular techniques that may be used for confirmation of the presence of a given locus and thus conversion of that locus.

The present invention additionally provides, in an embodiment, processes of preparing sorghum plant of variety GSV644454. In accordance with such an embodiment, a first parent sorghum plant may be crossed with a second parent sorghum plant wherein at least one of the first and second sorghum plants is the inbred sorghum plant GSV644454. One application of the process is in the production of $F_1$ hybrid plants. Another important aspect of this process is that it can be used for the development of novel inbred lines. For example, the inbred sorghum plant GSV644454 could be crossed to any second plant and the resulting hybrid progeny each selfed for about 5 to 7 or more generations, thereby providing a large number of distinct, pure-breeding inbred lines. These inbred lines could then be crossed with other inbred or non-inbred lines and the resulting hybrid progeny analyzed for beneficial characteristics. In this way, novel inbred lines conferring desirable characteristics could be identified. After at least five or more generations, the inbred plant is typically considered genetically pure. Thus, in an embodiment, the invention comprises genetically pure inbred lines produced from the inbred sorghum plant GSV644454.

In a particular embodiment of the invention, the genetic complement of the sorghum plant variety designated GSV644454 is provided. A genetic complement represents the genetic makeup of an inbred cell, tissue or plant. A hybrid genetic complement represents the genetic makeup of a hybrid cell, tissue or plant. The invention thus provides sorghum plant cells that have a genetic complement in accordance with the inbred sorghum plant cells disclosed herein, and plants, seeds and diploid plants containing such cells.

In still another embodiment, the present invention provides hybrid genetic complements, as represented by sorghum plant cells, tissues, plants, and seeds, formed by the combination of a haploid genetic complement of an inbred sorghum plant of the invention with a haploid genetic complement of a second sorghum plant, which may be another, distinct inbred sorghum plant. In another aspect, the present invention provides a sorghum plant regenerated from a tissue culture that comprises a hybrid genetic complement of this invention.

Plant genetic complements may be assessed by genetic marker profiles, and by the expression of phenotypic traits that are characteristic of the expression of the genetic complement, e.g., isozyme typing profiles. It is understood that the sorghum variety designated GSV644454 could be identified by any of the many known techniques such as, for example, Simple Sequence Length Polymorphisms, Randomly Amplified Polymorphic DNAs, DNA Amplification Fingerprinting, Sequence Characterized Amplified Regions, Arbitrary Primed Polymerase Chain Reaction, AFLPs, and SNPs.

A genetic marker profile of an inbred may be predictive of the agronomic traits of a hybrid produced using that inbred. For example, if an inbred of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data are known in the art. Such predictions may be made using any suitable genetic marker, for example, SSRs, RFLPs, AFLPs, SNPs, or isozymes.

SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by PCR, thereby eliminating the need for labor-intensive Southern hybridization. PCR detection is conducted using two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology. Following amplification, markers can be scored by gel electrophoresis of the amplification products. Scoring of marker genotype is based on the size (number of base pairs) of the amplified segment.

In another embodiment of the invention, the method relates to the production of a sorghum plant of GSV644454 product. The sorghum plant product may be selected from the group consisting of starch, syrup, protein, or any other product known in the art to be made from sorghum plants or plant parts.

A deposit was made of at least 2500 seeds of sorghum variety GSV644454 with the American Type Culture Collection (ATCC), 10801 University Boulevard, Manassas, Va. 20110-2209 USA. The deposit was assigned ATCC Accession No. PTA-125098. The date of deposit of the seeds with the ATCC was May 4, 2018. The deposit will be maintained in the ATCC depository for a period of 30 years, or 5 years after the most recent request, or for the enforceable life of the patent, whichever is longer, and will be replaced if necessary during that period. Upon issuance, all restrictions on the availability to the public of the deposit will be irrevocably removed consistent with all of the requirements of the Budapest Treaty and 37 C.F.R. §§ 1.801-1.809. Applicant does not waive any infringement of rights granted under this patent or under the Plant Variety Protection Act (7 USC 2321 et seq.).

All references cited in this specification, including without limitation, all papers, publications, patents, patent applications, presentations, texts, reports, manuscripts, brochures, books, internet postings, journal articles, and/or periodicals are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the versions contained therein.

What is claimed is:

1. A plant of sorghum variety GSV644454, wherein representative seed of sorghum variety GSV644454 has been deposited under ATCC Accession No. PTA-125098.

2. A plant part of the plant of claim 1.

3. The plant part of claim 2, further defined as pollen, an ovule, or a cell.

4. A seed of sorghum variety GSV644454, wherein representative seed of sorghum variety GSV644454 has been deposited under ATCC Accession No. PTA-125098.

5. The seed of claim 4, further comprising a transgene, wherein the transgene was introduced into sorghum variety GSV644454 by backcrossing or genetic transformation.

6. A composition comprising the seed of claim 4 comprised in plant seed growth media, wherein representative seed of sorghum variety GSV644454 has been deposited under ATCC Accession No. PTA-125098.

7. The composition of claim 6, wherein the growth media is soil or a synthetic cultivation medium.

8. An F1 hybrid seed produced by crossing a plant of sorghum variety GSV644454 according to claim 1 with a second, distinct sorghum plant.

9. The F1 hybrid seed of claim 8, wherein said plant of sorghum variety GSV644454 further comprises a transgene that is inherited by the seed, wherein the transgene was introduced into sorghum variety GSV644454 by backcrossing or genetic transformation.

10. An F1 hybrid plant grown from the seed of claim 8.

11. A plant of sorghum variety GSV644454 further comprising a single locus conversion, wherein said plant otherwise comprises all of the morphological and physiological characteristics of sorghum variety GSV644454 when grown under the same environmental conditions, and wherein representative seed of sorghum variety GSV644454 has been deposited under ATCC Accession No. PTA-125098.

12. The plant of claim 11, wherein the single locus conversion comprises a transgene.

13. A seed that produces the plant of claim 11.

14. The seed of claim 13, wherein the single locus confers a trait selected from the group consisting of male sterility, herbicide tolerance, insect or pest resistance, disease resistance, modified fatty acid metabolism, abiotic stress resistance, altered seed amino acid composition, site-specific genetic recombination, and modified carbohydrate metabolism.

15. The seed of claim 14, wherein the herbicide tolerance trait confers tolerance to imidazolinone herbicides, sulfonylurea herbicides, triazine herbicides, phenoxy herbicides, cyclohexanedione herbicides, benzonitrile herbicides, 4-hydroxyphenylpyruvate dioxygenase-inhibiting herbicides, protoporphyrinogen oxidase-inhibiting herbicides, acetolactate synthase-inhibiting herbicides, 1-aminocyclopropane-1-carboxylic acid-inhibiting herbicides, bromoxynil, nicosulfuron, 2,4-dichlorophenoxyacetic acid (2,4-D), dicamba, quizalofop-p-ethyl, glyphosate, or glufosinate.

16. A method of producing a progeny sorghum plant, said method comprising applying plant breeding techniques to the plant of claim 1 or an F1 hybrid thereof to yield said progeny sorghum plant.

17. The method of claim 16, wherein the plant breeding techniques comprise backcrossing, marker assisted breeding, pedigree breeding, selfing, outcrossing, haploid production, doubled haploid production, or transformation.

18. The method of claim 16, further defined as comprising:
   (a) crossing the plant of claim 1 or an F1 hybrid thereof with itself or a second plant to produce a seed of a progeny plant of a subsequent generation;
   (b) growing a progeny plant of a subsequent generation from said seed and crossing the progeny plant of a subsequent generation with itself or a second plant; and
   (c) repeating steps (a) and (b) with sufficient inbreeding until an inbred sorghum plant is produced.

19. A method of producing a commodity plant product, said method comprising obtaining the plant of claim 1 or a part thereof and producing said commodity plant product therefrom.

20. The method of claim 19, wherein the commodity plant product is grain, starch, seed oil, sorghum syrup, or protein.

* * * * *